US012758599B2

(12) United States Patent
Nakajima et al.

(10) Patent No.: US 12,758,599 B2
(45) Date of Patent: Oct. 13, 2026

(54) COMPOSITION FOR INHIBITION OF DIFFERENTIATION OF OSTEOCLAST PRECURSOR CELLS INTO OSTEOCLASTS, AND COMPOSITION FOR IMPROVING BONE METABOLISM

(71) Applicant: HOUSE WELLNESS FOODS CORPORATION, Hyogo (JP)

(72) Inventors: Tsubasa Nakajima, Hyogo (JP); Kohei Kitamura, Hyogo (JP); Hiroko Nakai, Hyogo (JP); Yoshitaka Hirose, Hyogo (JP)

(73) Assignee: HOUSE WELLNESS FOODS CORPORATION, Hyogo (JP)

( * ) Notice: Subject to any disclaimer, the term of this patent is extended or adjusted under 35 U.S.C. 154(b) by 307 days.

(21) Appl. No.: 18/561,110

(22) PCT Filed: Mar. 22, 2022

(86) PCT No.: PCT/JP2022/013051
§ 371 (c)(1),
(2) Date: Nov. 15, 2023

(87) PCT Pub. No.: WO2022/244447
PCT Pub. Date: Nov. 24, 2022

(65) Prior Publication Data

US 2024/0252559 A1 Aug. 1, 2024

(30) Foreign Application Priority Data

May 17, 2021 (JP) ................................ 2021-083347

(51) Int. Cl.
*A61K 35/747* (2015.01)
*A61P 19/10* (2006.01)

(52) U.S. Cl.
CPC ............ *A61K 35/747* (2013.01); *A61P 19/10* (2018.01)

(58) Field of Classification Search
CPC ........ A61P 19/08; A61P 19/10; A61K 35/747; C12N 5/0654
See application file for complete search history.

(56) References Cited

U.S. PATENT DOCUMENTS

| | | | |
|---|---|---|---|
| 2010/0098728 A1 | 4/2010 | Fujiki et al. | |
| 2020/0353020 A1 | 11/2020 | Nakai et al. | |

FOREIGN PATENT DOCUMENTS

| | | |
|---|---|---|
| AU | 2015268629 A * | 1/2016 |
| CN | 103037882 | 12/2014 |
| CN | 105188723 | 12/2015 |
| CN | 108467843 | 8/2018 |
| JP | 11-228425 | 8/1999 |
| JP | 2010-6801 | 1/2010 |
| JP | 2010-95465 | 4/2010 |
| JP | 2010-235534 | 10/2010 |
| JP | 2015-96476 | 5/2015 |
| JP | 2017-114814 | 6/2017 |
| KR | 10-1554875 | 9/2015 |
| KR | 2016-0086249 | 7/2016 |
| WO | 2013/176327 | 11/2013 |
| WO | 2019/045037 | 3/2019 |

OTHER PUBLICATIONS

Kuo et al., Biomarker Research, 2017; 5(18): 1-9 (Year: 2017).*
Choi et al., npj Metabolic Health and Disease, 2024; 2(12): 1-10 (Year: 2024).*
Osteoporosis, Cleveland Clinic, https://my.clevelandclinic.org/health/diseases/4443-osteoporosis; last reviewed on Jul. 20, 2023 (Year: 2023).*
Collins et al., Scientific Reports, 2019; 9(14708): 1-14 (Year: 2019).*
English-language version of International Preliminary Report on Patentability issued Nov. 21, 2023 in International (PCT) Application No. PCT/JP2022/013051.
Extended European Search Report issued Mar. 26, 2025 in corresponding European Patent Application No. 22804365.9.
Ayako Uchinaka, et al.,"Anti-inflammatory effects of heat-killed Lactobacillus plantarum L-137 on cardiac and adipose tissue in rats with metabolic syndrome", Scientific Reports. vol. 8, No. 8156. May 25, 2018, pp. 1-20.
Chengxiang Li, et al., "The Role of Intestinal Flora in the Regulation of Bone Homeostasis", Frontiers in Cellular and Infection Microbiology. vol. 11. Mar. 12, 2021, pp. 1-16.
Extended European Search Report issued Apr. 20, 2026 in European Patent Application No. 26151145.5.
Place David E. et al: "Osteoclast fusion and bone loss are restricted by interferon inducible guanylate binding proteins", Nature Communications, vol. 12, No. 1, Jan. 21, 2021 (Jan. 21, 2021).
International Search Report issued Jun. 7, 2022 in International (PCT) Application No. PCT/JP2022/013051.
Kimoto, Hiromi, "Potential probiotic lactic acid bacterium Lactococcus lactis H61 contributing to high quality of life", Japanese Journal of Lactic Acid Bacteria, 2018, 29(2) pp. 69-78 (with partial English translation).

(Continued)

*Primary Examiner* — Brian Gangle
*Assistant Examiner* — Lakia J Jackson-Tongue
(74) *Attorney, Agent, or Firm* — Wenderoth, Lind & Ponack, L.L.P.

(57) ABSTRACT

A problem to be solved by the present invention is to provide a composition (1) for inhibiting differentiation of osteoclast precursor cells into osteoclasts, improving bone metabolism, and/or inhibiting bone density reduction, the composition (1) including a culture supernatant or a processed product thereof, the culture supernatant being obtainable by culturing immune cells in the presence of lactic acid bacteria or a processed product thereof, or a composition (2) for inhibiting differentiation of osteoclast precursor cells into osteoclasts, improving bone metabolism, and/or inhibiting bone density reduction, the composition (2) including *Lactobacillus plantarum* strain L-137 (*Lactobacillus plantarum* L-137) or a processed product thereof. These compositions solve the problem.

7 Claims, 3 Drawing Sheets

(56) References Cited

OTHER PUBLICATIONS

Office Action issued Feb. 11, 2026 in the corresponding Chinese Patent Application No. 202280032086.9, with English translation.
Zhong Yisheng et al., "Neovascular Ophthalmopathy", People's Military Medical Press, 2006, pp. 155.
Sun Lingyun, "Molecular Rheumatology", Inner Mongolia People's Publishing House, 1997, pp. 49.
Zhao Jiajun et al., "Systemic Endocrinology (vol. II)" China Science and Technology Press, 2021, pp. 1109.
Xu Youjia, "Iron Metabolism and Osteoporosis", Soochow University Press, 2016, pp. 67.

* cited by examiner

COMPOSITION FOR INHIBITION OF DIFFERENTIATION OF OSTEOCLAST PRECURSOR CELLS INTO OSTEOCLASTS, AND COMPOSITION FOR IMPROVING BONE METABOLISM

TECHNICAL FIELD

The present invention relates to a composition for inhibiting differentiation of osteoclast precursor cells into osteoclasts, and a composition for improving bone metabolism.

BACKGROUND ART

Osteoporosis is a disease that causes bone fragilization that is often associated with proneness to bone fractures. There are two types of cells in bones, namely osteoblasts for bone formation and osteoclasts for bone absorption. The balance between activities of the osteoblasts and osteoclasts would be lost due to activation of the osteoclasts or the other reasons. Prolonged quantitative overbalancing of the bone absorption over the bone formation would result in bone mass reduction, which would develop osteoporosis. In Japan, about 10 million or more people are suffering from osteoporosis and the number of the patients of osteoporosis is on the rise along the aging of the population. As one of methods for improving osteoporosis, it has been known to inhibit differentiation of osteoclast precursor cells (precursor cells of osteoclasts) into osteoclasts (Patent literature 1).

Meanwhile, it is known that lactic acid bacteria have an immunostimulatory effect and the like (Patent literature 2).

CITATION LIST

Patent Literatures

Patent literature 1: JP 2010-235534 A
Patent literature 2: JP 2010-6801 A

SUMMARY OF INVENTION

Technical Problem

So far there is no report that a culture supernatant of immune cells obtainable via culturing of the immune cells in the presence of lactic acid bacteria or a processed product thereof can inhibit the differentiation of osteoclast precursor cells into osteoclasts or improve the bone metabolism. Furthermore, so far there is no report that the lactic acid bacteria *Lactobacillus plantarum* strain L-137 (*Lactobacillus plantarum* L-137, which may be referred to as "L-137 strain") has effects similar to those of the culture supernatant of the immune cells described above.

Solution to Problem

The present inventors found that (1) a culture supernatant of a culture obtainable by culturing immune cells in the presence of lactic acid bacteria or a processed product thereof has an inhibitory effect on differentiation of osteoclast precursor cells into osteoclasts, an improving effect on the bone metabolism, and/or an inhibitory effect on the bone density reduction, and preferably an inhibitory effect on the bone absorption characteristics in bones. Furthermore, the present inventors found that (2) the lactic acid bacteria *Lactobacillus plantarum* strain L-137 has effects similar to those of the culture supernatant of (1), and that (3) the culture supernatant of (1) and L-137 strain of (2) are effective for treatment or prevention of osteoporosis or the like. The inventors carried out further studies and completed the present invention.

That is, the present invention includes the following.

(1) A composition for inhibiting differentiation of osteoclast precursor cells into osteoclasts, the composition comprising a culture supernatant or a processed product thereof, the culture supernatant being obtainable by culturing immune cells in the presence of lactic acid bacteria or a processed product thereof.

(2) A composition for improving bone metabolism, the composition comprising a culture supernatant or a processed product thereof, the culture supernatant being obtainable by culturing immune cells in the presence of lactic acid bacteria or a processed product thereof.

(3) The above composition according to (1) or (2), wherein the lactic acid bacteria are *Lactobacillus* bacteria.

(4) The above composition according to any one of (1) to (3), wherein the lactic acid bacteria are *Lactobacillus plantarum* strain L-137 (*Lactobacillus plantarum* L-137).

(5) A composition for inhibiting differentiation of osteoclast precursor cells into osteoclasts, the composition comprising *Lactobacillus plantarum* strain L-137 (*Lactobacillus plantarum* L-137) or a processed product thereof.

(6) A composition for improving bone metabolism, the composition comprising *Lactobacillus plantarum* strain L-137 (*Lactobacillus plantarum* L-137) or a processed product thereof.

(7) The above composition according to any one of (1) to (6), wherein the composition is for preventing, improving, and/or treating osteoporosis.

(8) The above composition according to any one of (1) to (7), wherein the composition is for inhibiting bone density reduction.

(9) A method of producing a composition for inhibiting differentiation of osteoclast precursor cells into osteoclasts, improving bone metabolism, and/or inhibiting bone density reduction, the method comprising:

(a) preparing a culture by culturing immune cells in the presence of lactic acid bacteria or a processed product thereof;

(b) preparing a culture supernatant of the immune cells or a processed product thereof, the step (b) including removing the lactic acid bacteria or the processed product thereof, and the immune cells from the culture prepared in step (a); and (c) mixing the culture supernatant or the processed product thereof prepared in the step (b) with a carrier and/or an excipient.

Advantageous Effects of Invention

According to the present disclosure, it is possible to provide a composition for inhibiting the differentiation of osteoclast precursor cells into osteoclasts, a composition for improving the bone metabolism, and/or a composition for inhibiting the bone density reduction, and preferably a composition for preventing, improving, or treating osteoporosis. Moreover, according to the present disclosure, it is possible to provide a method for producing such a composition.

Figure 1:
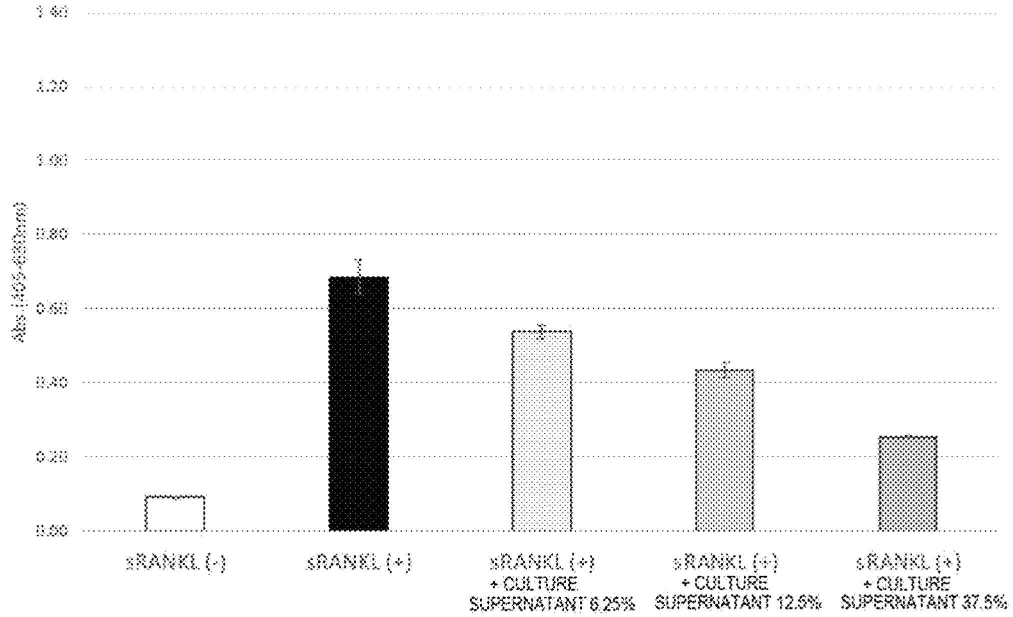
FIG. 1 is a graph evaluating inhibitory effects on differentiation of osteoclast precursor cells into osteoclasts and bone absorption activity 48 hours after addition of sRANKL (bone metabolism research reagent) and a culture supernatant of immune cells to the osteoclast precursor cells.

DESCRIPTION OF EMBODIMENTS (1) Culture Supernatant of Immune Cells or Processed Product Thereof The present invention encompasses a composition for inhibiting differentiation of osteoclast precursor cells into osteoclasts and a composition for improving bone metabolism, especially preferably a composition for inhibiting bone absorption, the compositions including a culture supernatant of immune cells or a processed product thereof, the culture supernatant being obtainable by culturing a mixture of the immune cells and lactic acid bacteria or a processed product thereof, but the compositions preferably substantially excluding the lactic acid bacteria or the processed product thereof used in obtaining the culture supernatant.

In the Description of the present application, the precursor cells of osteoclasts may be abbreviatedly referred to as "osteoclast precursor cells". Moreover, generally the "culture supernatant" herein means a supernatant liquid that has been separated, for example by centrifugal separation, from a culture prepared by culturing immune cells. Preferable conditions for the centrifugal separation may be, but not limited to, a temperature in a range of 1° C. to 40° C., preferably in a range of 4° C. to 37° C., a rotational speed in a range of 2000 to 20,000 rpm, and the like.

The lactic acid bacteria used in the present invention may be, but not limited to, lactic acid bacteria belonging to the genus *Lactobacillus, Streptococcus, Enterococcus. Lactococcus, Bifidobacterium*, etc. More specific examples of the lactic acid bacteria include, but are not limited to: *Lactobacillus plantarum, Lactobacillus acidophilus, Lactobacillus brevis, Lactobacillus casei, Lactobacillus fermentum, Lactobacillus paracasei, Lactobacillus buchneri, Lactobacillus delbrueckii*, or *Lactobacillus rhamnosus; Streptococcus thermophilus; Enterococcus faecalis*, or *Enterococcus faecium; Lactococcus lactis*, or *Lactococcus plantarum*; or *Bifidobacterium thermophilum, Bifidobacterium longum*, or *Bifidobacterium breve*; etc.

In the present invention, the immune cells may be preferably, but not limited to, cells including cells capable of ingesting (phagocytizing) the lactic acid bacteria described above, preferably cells including cells capable of ingesting lactic acid bacteria, *Lactobacillus plantarum*, or more preferably cells including cells capable of ingesting *Lactobacillus plantarum* L-137 (Accession Number: FERM BP-08607).

It is known that the L-137 strain has more lipoteichoic acid exposed on its cell surface than certain types of *Lactobacillus* lactic acid bacteria widely used in the field, for example, *Lactobacillus plantarum* JCM1149 and the like, and thereby is more easily ingestible for certain types of cells (see, Int Immunopharmacol. 2015, 25(2)321-331). While the detailed mechanisms thereof have been unknown yet, this feature of the L-137 strain would possibly usefully contribute to attaining the inhibitory effect of the present invention on the differentiation of osteoclast precursor cells into osteoclasts or the improving effect of the present invention on the bone metabolism.

Examples of preferable immune cells employable in the present invention include, but not limited to, cells including cells such as macrophages, natural killer (NK) cells, dendritic cells, B cells, and T cells. The immune cells may be one commercially available. Examples of commercially available immune cells include, but not limited to, IQB-MSP103 available from iQ Biosciences, and products available from Charles River Laboratories Japan, Inc., CLEA Japan. Inc., or the other suppliers.

Moreover, preferable osteoclast precursor cells used in the present invention may be preferably cells inducible to differentiation into osteoclasts with a reagent such as RANKL (receptor activator of NF-κB ligand) or GM-CSF (Granulocyte Macrophage colony-stimulating Factor), and examples of the osteoclast precursor cells include, but not limited to, primary cells of monocytes derived from bone marrow, macrophage progenitor cells, and macrophage-like cells, and cell lines thereof.

In the following, a method of culturing immune cells in the presence of lactic acid bacteria or a processed product thereof will be described. The culturing method of the immune cells is such that incubation temperature and incubation time are not particularly limited and may be selected as appropriate for the cells used. For example, the incubation temperature may be, but not limited to, a temperature preferably in a range of 30° C. to 40° C., or more preferably in a range of 35° C. to 37° C. For example, the incubation time may be, but not limited to, a time period preferably in a range of 24 to 96 hours, or more preferably in a range of 48 to 72 hours.

A medium used in the culturing of the immune cells is not particularly limited and may be preferably a medium containing an inorganic salt, a carbohydrate, an amino acid, a vitamin, a protein, a peptide, a fatty acid, a lipid, serum, and/or the like. The medium may be one commercially available. For example, preferable examples of well-known synthetic general media include, but not limited to, RPMI1640, DMEM, MEM, MEM α, IMDM, and McCoy's 5A.

The culturing method and medium for the osteoclast precursor cells may be preferably those exemplified for the immune cells above.

In the present invention, the "processed product" of the culture supernatant of the immune cells may be preferably, but not limited to, a product obtainable by preparing a culture of the immune cells according to the method of the present invention, purifying or processing the culture, and if necessary, subjecting the purified or processed culture to centrifugal separation. The purifying or processing of the culture thus prepared may include performing a well-known method in the field such as natural filtration, microfiltration, or ultrafiltration. Examples of preferable conditions of the centrifugal separation include, but not limited to, a temperature in a range of 1° C. to 40° C., or preferably in a range of 4° C. to 37° C., a rotational speed in a range of 2000 to 20,000 rpm, and the like. In general, the culture supernatant of the immune cells of the present invention or a processed product thereof substantially excludes the lactic acid bacteria or the processed product thereof, and the immune cells themselves used in obtaining the culture supernatant.

Moreover, the present invention may be such that the culture supernatant of the immune cells or the processed product thereof may be used in the form as prepared, or may be used in a powder form prepared by a method such as lyophilization, low-temperature drying, spray drying, L-drying, or any combination of them. Moreover, the processed product may be used after diluted with an appropriate solvent (such as water, alcohol, an organic solvent, or the like) or may be used after converted into a gel or a solid preparation by adding an appropriate additive thereto.

The amount of the culture supernatant of the immune cells or the processed product thereof in the composition of the present invention is not particularly limited, and may be, for example, in a range of about 0.1 to about 100 wt %, or preferably in a range of about 5 to about 40 wt % in the composition of 100 wt %.

(2) *Lactobacillus plantarum* Strain L-137

As some other aspects thereof, the present invention further encompasses a composition for inhibiting differentiation of osteoclast precursor cells into osteoclasts and a composition for improving the bone metabolism, the compositions including lactic acid bacteria, *Lactobacillus plantarum* strain L-137 (*Lactobacillus plantarum* L-137, Accession Number: FERM BP-08607).

The osteoclast precursor cells and immune cells here are as described in (1) above.

The lactic acid bacteria *Lactobacillus plantarum* strain L-137 (*Lactobacillus plantarum* L-137) used in the present invention were deposited with the International Patent Organism Depositary of the Incorporated Administrative Agency National Institute of Advanced Industrial Science and Technology (currently known as the International Patent Organism Depositary of the Incorporated Administrative Agency National Institute of Technology and Evaluation; address: #120, 2-5-8 Kazusakamatari, Kisarazu-shi, Chiba 292-0818, Japan) under Accession Number: FERM BP-08607 (transferred from FERM P-15317 deposited on Nov. 30, 1995). *Lactobacillus plantarum* L-137 herein includes mutants of *Lactobacillus plantarum* L-137 that have the same characteristics as those of *Lactobacillus plantarum* L-137. The compositions of the present invention may include other lactic acid bacteria together with the *Lactobacillus plantarum* strain L-137.

The amount of *Lactobacillus plantarum* strain L-137 (*Lactobacillus plantarum* L-137) or the processed product thereof in the compositions of the present invention may be in a range of about 0.0001 to 0.1 wt %, or preferably in a range of 0.005 to 0.05 wt % in the composition of 100 wt %, but not limited to these ranges.

The intake of *Lactobacillus plantarum* L-137 (*Lactobacillus plantarum* L-137) of the present invention, when administered orally or via an injection, can be determined depending on the age and body weight of the subject, the symptoms, the administration period, the dosage form, the mode of administration, a medicine to be co-administered, etc. For example, the intake of *Lactobacillus plantarum* L-137 based on the weight of the dried killed cells is preferably about 0.5 to 200 mg per adult human (about 60 kg) per day, more preferably about 1 to 100 mg per adult human (about 60 kg) per day, and further more preferably about 2 to 50 mg per adult human (about 60 kg) per day. The intake of *Lactobacillus plantarum* L-137 based on the number of the viable cells is preferably about $5\times10^8$ to $2\times10^{11}$ cfu (colony forming unit) per adult human (about 60 kg) per day, more preferably about $1\times10^9$ to $1\times10^{11}$ cfu per adult human (about 60 kg) per day. The frequency of intake may be once a day or dividedly multiple times a day. When administered via external application, the amount of *Lactobacillus plantarum* L-137 or the processed product thereof applied may be appropriately selected depending on the area of the skin to be treated. Typically, the amount of *Lactobacillus plantarum* L-137 or the processed product thereof applied is preferably about 0.01 to 2.5 mg, more preferably about 0.02 to 1 mg, per day for about 10 $cm^2$ of the applied site. The daily dose may be administered or applied as a single dose per day or as multiple divided doses per day.

In the following, the invention described in (1) and (2) above will be further described as to features commonly shared therebetween.

Culturing of Lactic Acid Bacteria

In the present invention, the *Lactobacillus plantarum* strain L-137 (*Lactobacillus plantarum* L-137) and said other lactic acid bacteria may be those cultured in a culture medium such as a natural medium, a synthetic medium and a semi-synthetic medium. The culturing of the lactic acid bacteria herein may be performed in accordance with a known method, a method known per se or an equivalent method thereof.

The culture medium can be any culture medium, and is preferably, for example, a culture medium containing a nitrogen source and/or a carbon source. The nitrogen source may be, for example, but is not limited to, meat extract, peptone, gluten, casein, yeast extract, amino acids, etc. The carbon source may be, for example, but is not limited to, glucose, xylose, fructose, inositol, maltose, starch syrup, malted rice soup, starch, bagasse, wheat bran, molasses, glycerol, etc. These can be used alone or in combination of two or more types.

The culture medium can further contain a mineral in addition to the nitrogen source and/or the carbon source. The mineral may be, for example, but is not limited to, ammonium sulfate, potassium phosphate, magnesium chloride, sodium chloride, iron, manganese, molybdenum, various types of vitamins. etc. These can be used alone or in combination of two or more types.

The incubation temperature and incubation time of *Lactobacillus plantarum* strain L-137 (*Lactobacillus plantarum* L-137) and said other lactic acid bacteria may be any temperature and time that allow the bacteria to be efficiently cultured. In an embodiment of the present invention, the incubation temperature may be, for example, typically about 25° C. to 40° C., preferably about 27° C. to 35° C., and the incubation time may be, for example, about 12 to 48 hours. In an embodiment of the present invention, the lactic acid bacteria may be cultured with aeration and shaking. The pH of the culture medium is not particularly limited, and in an embodiment of the present invention, the pH may typically be about 3 to 6, preferably about 4 to 6.

Processed Products of Lactic Acid Bacteria

A "processed product" of *Lactobacillus plantarum* strain L-137 (*Lactobacillus plantarum* L-137) and said other lactic acid bacteria is preferably, but not limited to, a processed product or a culture of the lactic acid bacteria. The lactic acid bacteria may be viable bacterial cells or killed bacterial cells, but killed bacterial cells are preferred due to stability, ease of handling, and other advantages. The killed bacterial cells are encompassed in the processed product thereof.

The processed product may be used in the form as prepared, or may be formed into a powder by lyophilization, low-temperature drying, spray drying, L-drying, or a combination thereof, according to the present invention. The processed product may be used after diluted in an appropriate solvent (water, an alcohol, an organic solvent, etc.), or may be used after formed into a gel or a solid preparation by addition of an appropriate additive.

Preparation methods for killed cells of *Lactobacillus plantarum* strain L-137 (*Lactobacillus plantarum* L-137) and said other lactic acid bacteria will be specifically described below.

The preparation methods for the killed bacterial cells may be any methods that do not impair the effects of the present invention. The killed bacterial cells may be prepared by, for example, (I) a method involving separating viable cells of the lactic acid bacteria from the culture liquid after the culturing, and performing sterilization to kill the viable bacterial cells to give killed bacterial cells, or (II) a method involving sterilizing the culture liquid containing viable cells of the lactic acid bacteria to kill the viable bacterial cells, and separating the killed bacterial cells from the culture liquid.

The separation method of the bacterial cells from the culture liquid may be done by any method usually employed in this field. Specifically, in an embodiment of the present invention, the bacterial cells may be separated from the culture liquid by, for example, removing the supernatant by centrifugation etc. In this embodiment, if desired, after the addition of distilled water to the culture liquid and the centrifugation for removal of the supernatant, distilled water may be added to the residue obtained by the removal of the supernatant and the resulting suspension may be further centrifuged, and this procedure may be repeated several times. In an embodiment of the present invention, the separation procedure may include filtration.

The sterilization method to kill the viable cells of *Lactobacillus plantarum* strain L-137 (*Lactobacillus plantarum* L-137) and said other lactic acid bacteria will be specifically described below. The sterilization method is not particularly limited, and the sterilization may be performed by, for example, heating, UV irradiation, formalin treatment, etc. The sterilization may be performed on harvested viable bacterial cells or on a culture liquid containing viable bacterial cells.

When the sterilization is performed by heating, the heating temperature may be, for example, but is not limited to, typically in a range of about 60° C. to 100° C., preferably in a range of about 70° C. to 90° C. The heating may be performed by those known in the art, and may be, for example, but is not limited to, a heater etc. The heating time may be any length of time that allows sterilization to be sufficiently complete, and heating may be performed, for example, typically for about 5 to 40 minutes, preferably for about 10 to 30 minutes, after the temperature reaches a desired level.

The killed bacterial cells prepared as above may be subjected to grinding, disruption or lyophilization to give processed killed bacterial cells. In the present invention, such processed killed bacterial cells are also suitable as killed bacterial cells.

Compositions for Inhibiting Differentiation of Osteoclast Precursor Cells into Osteoclasts. For Improving Bone Metabolism of Bones, for Preventing, Improving, or Treating Osteoporosis and/or the Like, or for Inhibiting Bone Density Reduction The compositions of the present invention have an inhibitory effect on the differentiation of osteoclast precursor cells into osteoclasts and/or an improving effect on the bone metabolism. Use of the compositions may be, but not limited to, preferably use for preventing, improving, or treating osteoporosis, osteogenesis imperfecta, hypercalcemia, osteomalacia, osteohalisteresis, osteolytic bone disease, osteonecrosis, rheumatoid arthritis, osteoarthritis, inflammatory arthritis, osteomyelitis, cancer, bone loss due to aging or the like, bone fracture, or lumbago, more preferably use for preventing, improving, or treating osteoporosis, rheumatoid arthritis, or bone fracture, or further preferably use for preventing, improving, or treating osteoporosis. Other or further preferable examples of the compositions of the present invention include, but not limited to, a composition having an inhibitory effect on the bone density reduction.

The composition of the present invention preferably serves as a food or a drink, and/or as a medicament (including a veterinary medicine), and in other preferred examples, the composition may serve as an additive for a food or a drink.

The composition serving as a food or a drink, an additive for a food or a drink, or a medicament can be formulated into a pharmaceutical formulation or the like by combining, as appropriate, the culture supernatant of the present invention or a processed product thereof, or the L-137 strain or a processed product thereof with a pharmaceutically acceptable carrier, additive, and/or the like. The formulation methods and formulation technology for preparing such a formulation are well established in the field, and the preparation of the formulation may be performed in accordance with such methods and technology. More specifically, for example, the composition serving as a medicament can be formulated into an oral formulation, such as a tablet, a coated tablet, a pill, a powder, granules, a capsule, a liquid, a suspension or an emulsion; or a parenteral formulation, such as an injection, an infusion, a suppository, an ointment or a patch. The blending ratio of the carrier or additive is determined as appropriate based on the amount of the carrier or additive usually used in the field of foods and drinks, medicaments or veterinary medicines.

The pharmaceutically acceptable carrier or additive is not limited to a particular one, and examples thereof include, but are not limited to, various types of carriers such as aqueous or oleaginous bases, and examples of aqueous carriers include, but not limited to, water, physiological saline, ethanol, glycerol, polyethylene glycol, propylene glycol, methyl cellulose, hydroxypropyl methylcellulose, hydroxypropyl cellulose, polyvinylpyrrolidone, polyacrylate, polysacchande gum-based natural polymers, and the like. Examples of the oleaginous carriers include, but not limited to, appropriate oils and waxes such as petroleum jelly, squalene, and paraffin.

Examples of additives include, but not limited to, enzymes, pH adjusting agents, preservatives, antimicrobial agents, antioxidants, antifungal agents, shelf life improvers, bleaching agents, brightening agents, fragrances and flavors, sweeteners, acidulants, seasonings and condiments, bittering agents, emulsifiers, thickeners, stabilizers, gelling agents, thickening agents, excipients, binders, disintegrants, lubricants, colorants, flavor improvers and fragrance and flavors. Techniques relating to such carriers or additives are well established in the art, and the carriers or additives can be used in accordance with such techniques.

When the composition of the present invention is for a food or a drink, the food or drink may be a health food, a food with functional claims, a food for specified health use, and a food for sick people. The form of the food or drink is not limited to a particular one, and specific examples thereof include tablets, granules, powders, energy drinks, etc. that are ingested as so-called nutritional supplements or dietary supplements. Other examples thereof include, but are not limited to, drinks such as tea drinks, soft drinks, carbonated drinks, nutritional drinks, fruit juices, and lactic drinks; noodles such as buckwheat noodles, wheat noodles, Chinese noodles, and instant noodles; sweets and bakery products such as drops, candies, gum, chocolate, snacks, biscuits, jellies, jams, creams, pastries, and bread; fishery and livestock products, such as hams, sausages, hanpen fish cakes, and chikuwa fish cakes; dairy products such as processed milk and fermented milk; fats, oils and processed foods thereof, such as vegetable oils, oils for deep frying, margarine, mayonnaise, shortening, whipping cream, and dressings; seasonings and condiments such as sauces and dipping sauces; retort pouch foods such as those of curry, stew, rice-bowl cuisine, porridge, and rice soup; and frozen desserts, such as ice creams, and sherbets. Techniques relating to such foods and drinks are well established in the art, and the foods and drinks can be produced and used in accordance with such techniques.

The composition of the present invention may further contain an ingredient known in the field of, for example, medicine, pharmaceuticals, veterinary medicine, livestock, feeds, foods, etc. to the extent that the effects of the present invention are not impaired.

Inhibitory Effect on the Differentiation of Osteoclast Precursor Cells into Osteoclasts and Improving Effect on Bone Metabolism, and Examination Thereof The effects of the compositions of the present invention can be confirmed by, for example, examining whether or not the compositions of the present invention including the culture supernatant or a processed product thereof, or *Lactobacillus plantarum* strain L-137 (*Lactobacillus plantarum* L-137) or a processed product thereof are more excellent in the inhibitory activity for the differentiation of osteoclast precursor cells into osteoclasts and/or the improving activity for the bone metabolism, compared with a composition not including either the culture supernatant or the processed product thereof or either the L-137 strain or the processed product thereof.

More specifically, examples of the method for examining the inhibitory effect on the differentiation of osteoclast precursor cells into osteoclasts and/or the improving effect on the bone metabolism include a method including adding a RANKL (receptor activator of NF-κB ligand) reagent to a sample and thereafter evaluating the sample in terms of TRAP (tartrate-resistant acid phosphatase) activity, and like method. The RANKL is known as a differentiation inducing signal and bonds to a receptor (RANK) on a cell membrane of the osteoclast precursor cells, thereby inducing the differentiation into osteoclasts. On the other hand, osteoclasts exhibit a high TRAP activity in the cytoplasm. Therefore, the differentiation into osteoclasts can be confirmed by evaluating the TRAP activity after the addition or administration of RANKL. That is, it can be said that the TRAP activity here serves as an indicator for the differentiation of osteoclast precursor cells into the osteoclasts. It is considered that the inhibition of the TRAP activity inhibits bone destruction, consequently improving the bone metabolism and, therefore, it is also considered the TRAP activity is effective for confirming whether or not osteoporosis is inhibited. In the Description of the present application, what is meant by the improvement of the bone metabolism is attaining a better balance between the bone formation and bone absorption in the body, for example.

Apart from that, a well-known reagent for bone evaluations or bone differentiation other than the one described above may be used. For example, the evaluation may be carried out by a method well-established in the art such as ELISA (Enzyme-Linked Immunosorbent Assay, in which a target antigen or antibody in a sample solution is captured with a specific antibody or antigen, and the target antigen or antibody thus captured is detected or quantified by using an enzyme reaction), and Bone resorption assay (pit formation assay).

As examples of such methods, Examples described later can be referred to.

Inhibitory Effect on Bone Density Reduction and Examination Thereof

Examples of a method for examining a composition of the present invention as to the inhibition of the bone density reduction include a method of confirming whether or not the composition including the culture supernatant or a processed product thereof, or *Lactobacillus plantarum* strain L-137 (*Lactobacillus plantarum* L-137) or a processed product thereof is more excellent in the inhibitory activity of the bone density reduction, compared with a composition excluding the culture supernatant or a processed product thereof, or *Lactobacillus plantarum* strain L-137 (*Lactobacillus plantarum* L-137) or a processed product thereof.

More specifically, examples of the method for examining the inhibitory effect on the bone density reduction include a method including measuring an ultrasonic propagation distance per unit time (m/sec), that is, measuring a speed of sound (SOS) in a bone.

This method is advantageous in that it does not involve radiation exposure and therefore is applicable even to measure pregnant women or children. Typically, the SOS is measured at a calcaneus bone, and has a high correlation with a bone density of a trabecular bone-rich region such as a calcaneus bone. A higher SOS value means a higher bone density. Because different measuring devices or different manufacturers thereof variously have different definitions of SOS or different reference values for SOS, a standardized-SOS (s-SOS) may be also used for securing compatibilities between measured values of different devices. In the present invention, for example, Benus evo (available from SHIBUYA CORPORATION) may be used, but another device well-known in the art may be used. In addition, there is a theory that the bone density solely accounts for the majority (about 70%) of bone strength. The method of the present invention is also effective for confirming whether osteoporosis is inhibited or not.

Apart from the SOS method descried above, which is classified as Quantitative Ultrasound (QUS) measurement, examples of applicable methods include a method of measuring Broadband Ultrasound Attenuation (BUA). Apart from the SOS measurement, the QUS measurement can be used for evaluation or the like of the composition according to the present invention. Moreover, other well-known bone density measurement methods than these described above, for example, Dual Energy X-ray Absorptiometry (DEXA), Microdensitometry (MD), Radiographic Absorptiometry (RA), Quantitative Computed Tomography (QCT), and the like, are also applicable to the present invention. The measurement may measure another region, such as, but not limited to, femur, vertebra, or radius, in addition to or instead of the calcaneus bone.

When the composition of the present invention is formulated into a food or a drink, a feed for an animal, a medicament (including a veterinary medicament) or a quasi-drug, the food or drink, feed for an animal, medicament, or quasi-drug, a package insert thereof, a package box or the like thereof, or the like may have an indication showing that the product has the inhibitory effect on the differentiation of osteoclast precursor cells into osteoclasts and the improving effect on the bone metabolism, based on the effects of the composition of the present invention.

The composition of the present invention may include the culture supernatant or the processed product thereof preferably by about 0.1 to 100 wt %, more preferably by about 5 to 60 wt %, or further preferably by about 20 to 40 wt % with respect to the entire amount of the composition.

Moreover, the compositions of the present invention may include *Lactobacillus plantarum* strain L-137 (*Lactobacillus plantarum* L-137) or a processed product thereof preferably by about 0.001 to 10 wt %, more preferably by about 0.01 to 1 wt %, or further preferably by about 0.05 to 0.5 wt % with respect to the entire amount of the composition.

Production Method of the Composition for Inhibiting the Differentiation of Osteoclast Precursor Cells into Osteoclasts and/or for Improving Bone Metabolism The present invention encompasses a method of producing a composition for inhibiting the differentiation of osteoclast precursor cells into osteoclasts and/or for improving bone metabolism, the method preferably including the following steps (a) to (c):

(a) preparing a culture by culturing immune cells in the presence of lactic acid bacteria or a processed product thereof;

(b) preparing a culture supernatant of the immune cells or a processed product thereof, the step (b) including removing the lactic acid bacteria or the processed product thereof, and the immune cells from the culture prepared in step (a); and (c) mixing the culture supernatant or the processed product thereof prepared in the step (b) with a carrier and/or an excipient.

The step (a) may include contacting a culture liquid including immune cells with lactic acid bacteria or a processed product thereof so as to prepare a mixture, wherein the immune cells may be especially preferably, but not limited to, immune cells capable of ingesting (phagocytizing) the lactic acid bacteria or the processed product thereof (preferably the L-137 strain).

Moreover, the step (b) may be arranged to remove the lactic acid bacteria or the processed product thereof and the immune cells from the mixture prepared in the step (a), wherein the removing the lactic acid bacteria or the processed product thereof, and the immune cells from the mixture may be performed by, but not limited to, a well-known method in the art such as centrifugal separation.

Furthermore, as to carriers employable in the step (c), preferable carriers have been well-established in the field of foods and pharmaceuticals, and such carriers can be adopted in the present invention. Examples of the carriers employable in the step (c) include various carriers such as aqueous or oleaginous bases, and examples of aqueous carriers include, but not limited to, water, physiological saline, ethanol, glycerol, polyethylene glycol, propylene glycol, methyl cellulose, hydroxypropyl methylcellulose, hydroxypropyl cellulose, polyvinylpyrrolidone, polyacrylate, polysaccharide gum-based natural polymers, and the like. Examples of the oleaginous carriers include, but not limited to, appropriate oils and waxes such as petroleum jelly, squalene, and paraffin.

Furthermore, as to excipients employable in the step (c), preferable excipients have been well-established in the field of foods and pharmaceuticals, and such excipients can be adopted in the present invention. Examples of the excipients preferably employable in the step (c) include, but not limited to, lactose, sucrose, mannitol, cone starch, powered cellulose, calcium hydrogen phosphate, and calcium carbonate.

The compositions of the present invention may be appropriately processed and produced according to a typical method for producing a composition, as long as the producing or processing includes adding the culture supernatant or the processed product thereof, or *Lactobacillus plantarum* strain L-137 (*Lactobacillus plantarum* L-137) or the processed product thereof to the composition. That is, the present invention encompasses a method for producing a composition, the method including mixing a culture supernatant or a processed product thereof, and if desired, another component. As an alternative, the present invention encompasses a method for producing a composition, the method including mixing *Lactobacillus plantarum* strain L-137 (*Lactobacillus plantarum* L-137) or the processed product thereof, and if desired, another component.

In the step of mixing a culture supernatant or a processed product thereof, and if desired, another component or mixing *Lactobacillus plantarum* strain L-137 (*Lactobacillus plantarum* L-137) or the processed product thereof, and if desired, another component, it is preferable that the mixing or stirring be performed according to a well-known method or a method known per se, so that the composition becomes wholly homogeneous as to the components thereof mixed together. Methods for mixing or stirring have been well established in the art and therefore the mixing or stirring herein may be performed according to such methods.

EXAMPLES

The present invention will be described more specifically with reference to the following examples and experiment examples, but the present invention is not limited thereto.

Experiment Example 1: Evaluation of Inhibition of the Differentiation of Osteoclast Precursor Cells into Osteoclasts and Inhibition of the Bone Absorption Activity by the Culture Supernatant Examination Method: 1. Step of Preparing the Culture Supernatant Immune cells (murine-derived spleen cells purchased from CLEA Japan, Inc.) were suspended in a 10% FBS-containing RPMI 1640 medium to a cell concentration of $5.0\times10^6$ cells/mL, thereby preparing an immune cell suspension. Dead cell components of *Lactobacillus plantarum* strain L-137 (*Lactobacillus plantarum* L-137) were suspended in a 10% FBS-containing RPMI 1640 medium to a concentration of 1000 ng/mL, thereby preparing an immune cell stimulation test liquid. The immune cell suspension and the immune cell stimulation test liquid, 100 μL each, were seeded in a 96-well culture plate (immune cells final concentration: $2.5\times10^6$ cells/mL, L-137 strain final concentration: 500 ng/ml) and incubated in an incubator under 5% $CO_2$ at 37° C. for 24 hours, thereby obtaining a supernatant. The supernatant thus obtained was subjected to centrifugal separation (conditions: 20° C., 2,000 rpm, 20 min), thereby obtaining a culture supernatant from which the L-137 strain and the immune cells had been removed.

2. Step of Inducing Differentiation of Osteoclast Precursor Cells into Osteoclasts The osteoclast differentiation was evaluated, using osteoclast precursor cells RAW264.7 (ECACC Cell Line No. 91062702; DS Pharma Biomedical Co., Ltd.), which is a murine-derived monocytic leukemia cell line that can be induced to osteoclasts with RANKL alone. Cells of osteoclast precursor cells RAW264.7 were suspended in 10% FBS-containing MEM α medium at $7.0\times10^4$ cells/mi and seeded in a 96-well culture plate at 50 μL thereof per well (3,500 cells/well). Furthermore, sRANKL (Product Number: 47187000; Oriental Yeast Co., Ltd.) was diluted with 10% FBS-containing MEM α medium at 267 ng/mL, and 75 μL of the diluted sRANKL was added to the 96-well culture plate per well on which the cells RAW264.7 had been seeded. Furthermore, the culture supernatant of the immune cells stimulated with L-137 strain was added thereto by 12.5 μL, 25 μL, or 75 μL. The total well content was made up to 200 μL by adding 62.5 μL of 10% FBS-containing MEM α medium into the wells with 12.5 μL of the culture supernatant added therein, and 50 μL of 10% FBS-containing MEM α medium into the wells with 25 μL of the culture supernatant added therein. That is, with the final concentration of sRANKL of 100 ng/mL, and the percentages of the immune cells in the culture supernatant of 6.25%, 12.5%, and 37.5% (v/v), the differentiation induction culturing was conducted in an incubator under 5% $CO_2$ at 37° C. for 48 or 72 hours.

3. Step of Measuring TRAP Activity

After the differentiation induction culturing, the supernatant was removed and 100 μL of a fixative solution in which acetone and ethanol were mixed at a ratio of 1:1 was added per well on the 96-well culture plate containing the cells. One minute after the addition, the fixative solution was removed from the plate and the plate was air-dried for 30 min. Thereafter, the plate was handled according to a TRAP solution kit (Product number; NIB 47249000; Oriental Yeast Co., Ltd.), and absorbance thereof was measured at 415 nm by using a plate reader.

Figure 2:
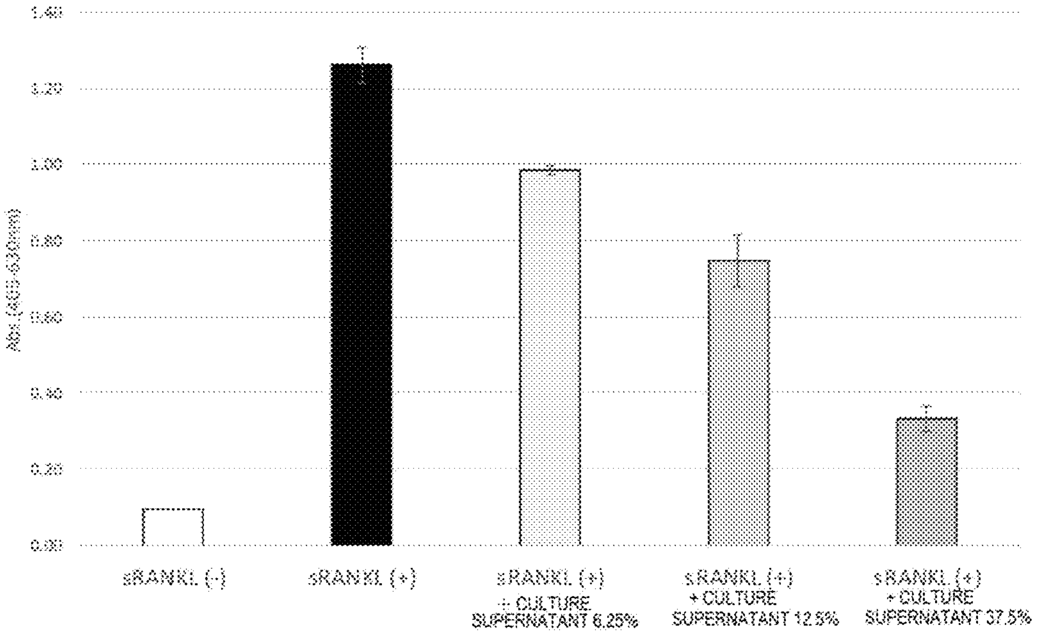
FIG. 2 is a graph evaluating the inhibitory effects on the differentiation of osteoclast precursor cells into osteoclasts and the bone absorption activity 72 hours after the addition of sRANKL (bone metabolism research reagent) and the culture supernatant of the immune cells to the osteoclast precursor cells.

Results: Evaluation results are listed on Table 1 and illustrated in FIGS. 1 and 2. After the 48-hour incubation and the 72-hour incubation, the culture supernatant of the immune cells obtained as above concentration-dependently exhibited the inhibitory effect on the differentiation of osteoclast precursor cells into osteoclasts and the inhibitory effect on the bone absorption in bones.

TABLE 1

| | TRAP Activities (Absorbance) | | Percentages against Control (%) | |
|---|---|---|---|---|
| | 48-hour Incubation | 72-hour Incubation | 48-hour Incubation | 72-hour Incubation |
| sRANKL(−) | 0.09 | 0.10 | 13% | 8% |
| sRANKL(+) | 0.69 | 1.26 | 100% | 100% |
| sRANKL(+) + Culture | 0.54 | 0.99 | 78% | 78% |
| Supernatant 6.25% | | | | |
| sRANKL(+) + Culture | | | 63% | |
| Supernatant 12.5% | 0.43 | 0.75 | | 59% |
| sRANKL(+) + Culture | | 0.33 | 37% | 27% |
| Supernatant 37.5% | 0.25 | | | |

Experiment Example 2: Evaluation of Inhibition of the Differentiation of Osteoclast Precursor Cells into Osteoclasts and Inhibition of the Bone Absorption Activity by the L-137 Strain Examination Method:

1. Step of Inducing Differentiation of Osteoclast Precursor Cells into Osteoclasts The osteoclast differentiation was evaluated, using osteoclast precursor cells RAW2647 (ECACC Cell Line No. 91062702: DS Pharma Biomedical Co., Ltd.), which is a murine-derived monocytic leukemia cell line and that can be induced to osteoclasts with RANKL alone. Cells of osteoclast precursor cells RAW264.7 were suspended in 10% FBS-containing MEM α medium at $7.0\times10^4$ cells/ml and seeded in a 96-well culture plate at 50 μL thereof per well (3,500 cells/well). Furthermore, sRANKL (Product Number: 47187000; Oriental Yeast Co., Ltd.) was diluted with 10% FBS-containing MEM α medium at 267 ng/mL, and 75 μL of the diluted sRANKL was added to the 96-well culture plate per well on which the cells RAW264.7 had been seeded. Furthermore, dead cell components of *Lactobacillus plantarum* strain L-137 (*Lactobacillus plantarum* L-137) were suspended in 10% FBS-containing MEM α medium at 134 ng/mL, 1.34 μg/mL, and 13.4 μg/mL, and 75 μL of the suspension was added per well on 96-well culture plate with the RAW 264.7 cells added therein, making up the total well content of 200 μL. That is, with the final concentration of the sRANKL of 100 ng/mL, and the final concentrations of the dead cell components of the L-137 strain of 50 ng/mL, 500 ng/mL, and 5 μg/mL, the differentiation induction culturing was conducted with the plate in an incubator under 5% $CO_2$ at 37° C. for 48 or 72 hours.

2. Step of Measuring TRAP Activity

After the differentiation induction culturing, the supernatant was removed and 100 μL of a fixative solution in which acetone and ethanol were mixed at a ratio of 1:1 was added per well on the 96-well culture plate containing the cells. One minute after the addition, the fixative solution was removed from the plate and the plate was air-dried for 30 min. Thereafter, the plate was handled according to the TRAP solution kit (Product number: NIB 47249000; Oriental Yeast Co., Ltd.), and absorbance thereof was measured at 415 nm by using the plate reader.

Figure 3:
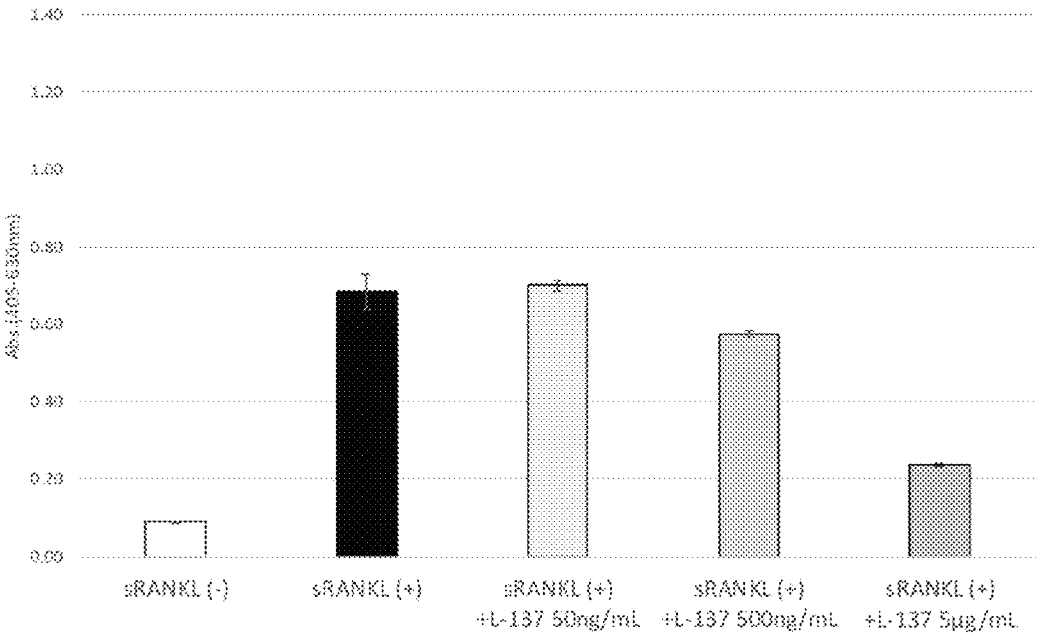
FIG. 3 is a graph evaluating the inhibitory effects on the differentiation of osteoclast precursor cells into osteoclasts and the bone absorption activity 48 hours after addition of sRANKL (bone metabolism research reagent) and the L-137 strain to the osteoclast precursor cells.
Figure 4:
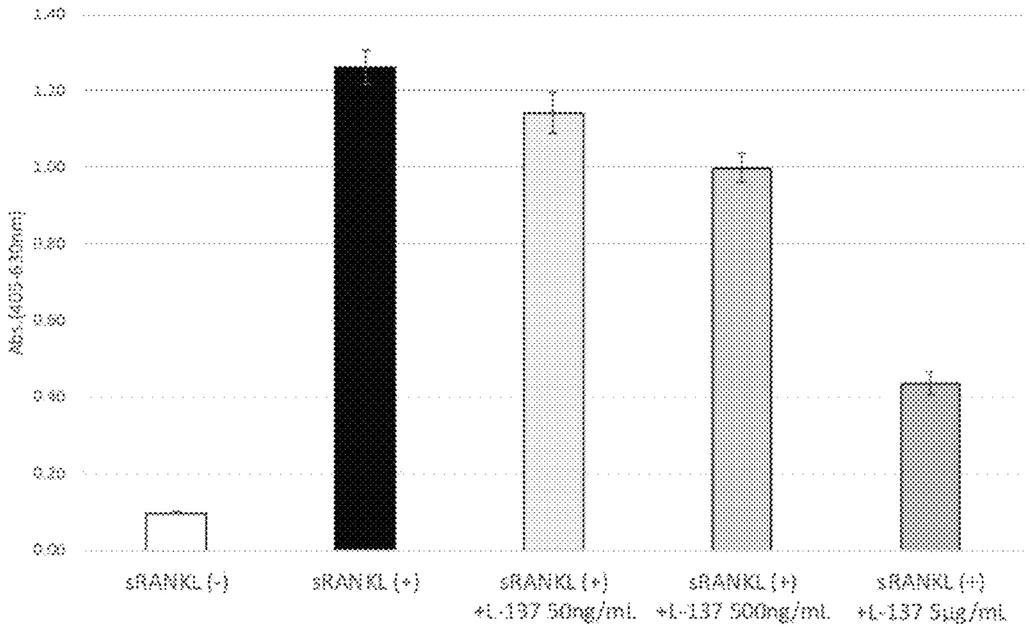
FIG. 4 is a graph evaluating the inhibitory effects on the differentiation of osteoclast precursor cells into osteoclasts and the bone absorption activity 72 hours after the addition of sRANKL (bone metabolism research reagent) and the L-137 strain to the osteoclast precursor cells.

Results: Evaluation results are listed on Table 2 and illustrated in FIGS. 3 and 4. After the 48-hour incubation and the 72-hour incubation, the lactic acid bacteria strain L-137 concentration-dependently exhibited the inhibitory effect on the differentiation of osteoclast precursor cells into osteoclasts and the inhibitory effect on the bone absorption in bones.

TABLE 2

| | TRAP Activities (Absorbance) | | Percentages against Control (%) | |
|---|---|---|---|---|
| | 48-hour Incubation | 72-hour Incubation | 48-hour Incubation | 72-hour Incubation |
| sRANKL(−) | 0.09 | 0.10 | 13% | 8% |
| sRANKL(+) | 0.69 | 1.26 | 100% | 100% |
| sRANKL(+) + L-137 50 ng/mL | 0.70 | 1.14 | 102% | 90% |

TABLE 2-continued

| | TRAP Activities (Absorbance) | | Percentages against Control (%) | |
|---|---|---|---|---|
| | 48-hour Incubation | 72-hour Incubation | 48-hour Incubation | 72-hour Incubation |
| sRANKL(+) + L-137 500 ng/mL | 0.57 | 1.00 | 84% | 79% |
| sRANKL(+) + L-137 5 μg/mL | 0.24 | 0.43 | 34% | 34% |

Experiment Example 3; Evaluation of Inhibitory Effect on the Bone Density Reduction by Composition Including Lactic Acid Bacteria Strain L-137

Examination Method: 1. Used Composition

As a composition of the present invention, a commercially available tablet containing 10 mg of heat-treated *Lactobacillus plantarum* strain L-137 per tablet (300 mg) (Product name: Manori-takarneru Lactic Acid Bacteria L-137 supplement) was used herein. The tablet also contains components other than the strain L-137 (such as lactose, starch, and sucrose fatty acid ester), but these other components do not affect the experiment described below.

2. Intake of the Composition and Measurement of s-SOS

Thirty-one human subjects, including males and females of ages ranging from 40 to 73 years were divided into 2 groups (non-intake group of 10 subjects and L-137 intake group of 21 subjects). The L-137 intake group was administered with the composition containing the L-137 strain by one tablet per day for a time period of 3 months.

The s-SOS of each subject was measured at the calcaneus bone before the start of the experiment and after the 3-month intake of the composition. A heel portion of one leg of a subject was washed with ethanol and applied sufficiently with an ultrasonic inspection jelly. After the jelly was thoroughly applied, the heel of the subject was brought into a measuring section of the device, and measured, thereby obtaining s-SOS reading.

The evaluation of the s-SOS at the calcaneus bones of the subjects was carried out with Benus evo (available from SHIBUYA CORPORATION).

Figure 5:
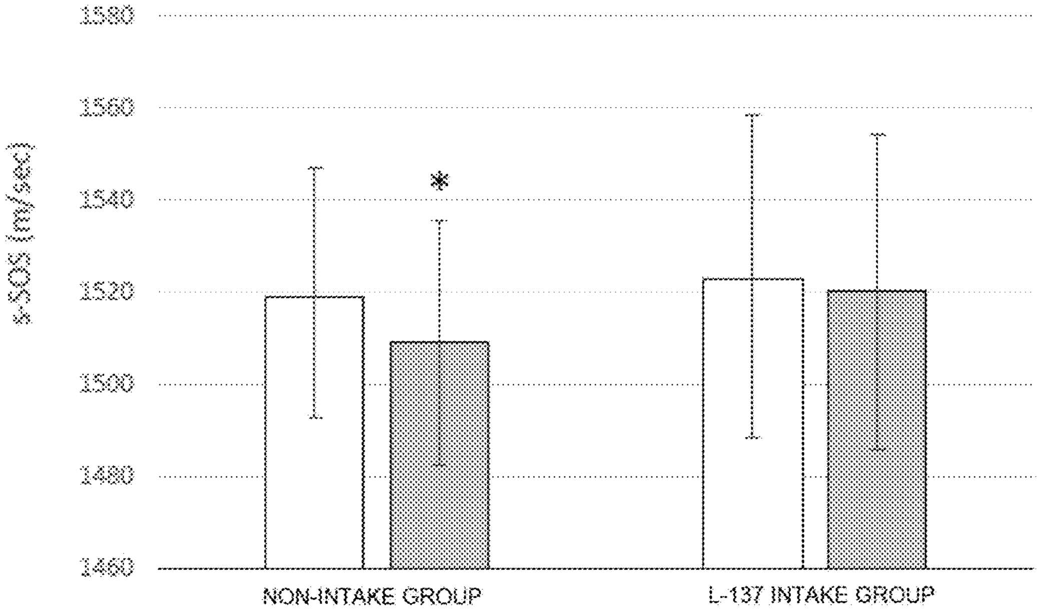
FIG. 5 is a graph evaluating an effect on the standardized speed of sound (s-SOS) through a human calcaneus bone with or without intake of a food containing the L-137 strain. The white bars indicate readings before the start of the experiment and the colored bars indicate readings measured after 3-month intake of the composition. Mean (+/−) SD, *: $p<0.05$ vs. before the start of the experiment.

Results: Evaluation results are illustrated in FIG. 5. The s-SOS values of the non-intake group were significantly reduced over the time period of 3 months from the start of the experiment (that is, their bone density was reduced). On the other hand, the s-SOS values of the L-137 intake group were not changed over the 3-month intake of the composition from the start of the experiment (that is, the bone density reduction was inhibited).

These results demonstrated that the lactic acid bacteria strain L-137-containing composition of the present invention exhibits an inhibitory effect on the bone density reduction. It should be noted that an effect similar thereto is also expectable in the case where the composition including the culture supernatant obtained according to the method in Experiment Example 1 or a processed product thereof is used in place of the L-137 strain.

INDUSTRIAL APPLICABILITY

Each of the composition (1) including the culture supernatant of immune cells according to the present invention and the composition (2) including the lactic acid bacteria strain L-137 independently exhibited an inhibitory effect on the differentiation of osteoclast precursor cells into osteoclasts, an improving effect on the bone metabolism, and/or an inhibitory effect on the bone density reduction. Therefore, each of the compositions (1) and (2) are usefully applicable to medicaments for preventing or treating osteoporosis, and foods, drinks, feeds, medicaments, quasi drugs, cosmetics, and the like.

The invention claimed is:

1. A method for inhibiting differentiation of osteoclast precursor cells into osteoclasts, the method comprising administering a culture supernatant to a subject, the culture supernatant being obtainable by culturing immune cells in the presence of *Lactobacillus plantarum* strain L-137 (*Lactobacillus plantarum* L-137, accession number FERM BP-08607) or the culture of said strain, wherein the immune cells comprise cells capable of ingesting lactic acid bacteria.

2. A method for inhibiting differentiation of osteoclast precursor cells into osteoclast, the method comprising administering *Lactobacillus plantarum* strain L-137 (*Lactobacillus plantarum* L-137, accession number FERM BP-08607) or the culture of said strain to a subject.

3. The method according to claim 1, wherein the method further includes improving, and/or treating osteoporosis.

4. The method according to claim 1, wherein the method further includes inhibiting bone density reduction.

5. A method of producing a composition for inhibiting differentiation of osteoclast precursor cells into osteoclasts, and/or inhibiting bone density reduction, the method comprising:

(a) preparing a culture by culturing immune cells in the presence of *Lactobacillus plantarum* strain L-137 (*Lactobacillus plantarum* L-137, accession number FERM BP-08607) ora the culture of said strain, wherein the immune cells comprise cells capable of ingesting lactic acid bacteria;

(b) preparing a culture supernatant of the immune cells, the step (b) including removing the *Lactobacillus plantarum* strain L-137 or the culture of said strain, and the immune cells from the culture prepared in step (a); and (c) mixing the culture supernatant prepared in the step (b) with a carrier and/or an excipient.

6. The method according to claim 2, wherein the method further includes improving, and/or treating osteoporosis.

7. The method according to claim 2, wherein the method further includes inhibiting bone density reduction.

* * * * *